United States Patent [19]
Hoffman et al.

[11] Patent Number: 6,131,473
[45] Date of Patent: Oct. 17, 2000

[54] RETRACTABLE HUMIDITY SENSOR FOR USE IN CORROSION TEST CHAMBERS

[75] Inventors: Jay D. Hoffman, Bethlehem; Herbert E. Townsend, Center Valley, both of Pa.

[73] Assignee: Bethlehem Steel Corporation

[21] Appl. No.: 09/085,916

[22] Filed: May 28, 1998

[51] Int. Cl.$^7$ ............................ G01N 33/00; G01M 19/00
[52] U.S. Cl. ................... 73/866.5; 73/31.05; 73/29.01
[58] Field of Search ............... 73/866.5, 31.05, 73/335.02, 865.6, 86, 31.01, 31.02, 29.01, 29.02, 29.05, 335.03, 335.04, 335.05; 422/53; 436/6

[56] References Cited

U.S. PATENT DOCUMENTS

| | | | |
|---|---|---|---|
| 3,007,340 | 11/1961 | Kroftson | 73/866.5 |
| 3,259,466 | 7/1966 | Jacks, Jr. | 73/865.6 X |
| 3,643,508 | 2/1972 | Schneider . | |
| 3,813,943 | 6/1974 | Fradeneck . | |
| 3,832,882 | 9/1974 | Schoen, Jr | 73/29.02 X |
| 4,075,035 | 2/1978 | Trevedy | 136/210 |
| 4,275,592 | 6/1981 | Atwood et al. | 73/86 X |
| 4,327,586 | 5/1982 | Goddard | 73/866.5 |
| 4,346,611 | 8/1982 | Welker | 73/866.5 X |
| 4,404,284 | 9/1983 | Heider et al. | 73/31.05 |
| 4,471,664 | 9/1984 | Mailliet et al. | 73/863.11 |
| 4,794,804 | 1/1989 | Ishii | 73/865.6 |
| 4,889,483 | 12/1989 | Gentry | 432/49 |
| 5,042,294 | 8/1991 | Uzzell | 73/75 |
| 5,294,048 | 3/1994 | Kawasaki | 73/31.02 X |
| 5,385,060 | 1/1995 | Wang | 73/866.5 |
| 5,484,008 | 1/1996 | Thompson | 164/338.1 |
| 5,487,532 | 1/1996 | Lonardi et al. | 266/271 |
| 5,824,918 | 10/1998 | Zuk | 73/29.01 X |
| 5,922,939 | 7/1999 | Cota | 73/866.5 |

FOREIGN PATENT DOCUMENTS

| | | | |
|---|---|---|---|
| 137056 | 6/1986 | Japan | 73/31.05 |
| 105212 | 5/1991 | Japan | 73/866.5 |
| 1659783 | 6/1991 | U.S.S.R. | 73/23.2 |

OTHER PUBLICATIONS

The Harshaw Chemical Co. undated drawing labeled Exhibit A and considered by Applicant on p. 2, starting at line 3 of the specification. Published by, approximated, 1987 Month not given.

Liebisch Drawing No. 20107–1, Mar.13, 1991, Drawing No. 20107–11, Mar. 12, 1991, and attached Liebisch LEGENDE Seitenzahl (page No.) 6 and 9 dated Mar. 1, 1991.

Operating Instructions, Hygromess–Transmitters, No. 0111, 0600, Revision 03/88 pp. 1–28.

*Primary Examiner*—Thomas P. Noland
*Attorney, Agent, or Firm*—Harold I. Masteller, Jr.

[57] ABSTRACT

A sensor probe device for monitoring atmosphere within a chamber. The device includes a housing that extends through a wall of the chamber being monitored, and a tubular sleeve that is movably captured within the housing. The sleeve includes an open end for receiving a sensor probe, and a closed end having a plurality of radially spaced apertures that extend through the sleeve wall. The apertures provide an open ribbed portion that exposes the enclosed sensor probe to chamber atmosphere when the sleeve portion is inserted into the chamber. A drive mechanism is attached to either extend the open ribbed portion of the sleeve outward from its shielded position within the housing to an extended position within the chamber, or retract the sleeve portion from the chamber back into its shielded position within the housing. An air supply is provided to inject forced air into the sleeve to maintain sensor probe integrity by purging contaminates through a drain in the sleeve wall, and an external air wipe nozzle is attached to the closed end of the sleeve to provide an air flow along the sleeve to prevent chamber atmosphere from entering the sleeve through the radially spaced apertures.

13 Claims, 4 Drawing Sheets

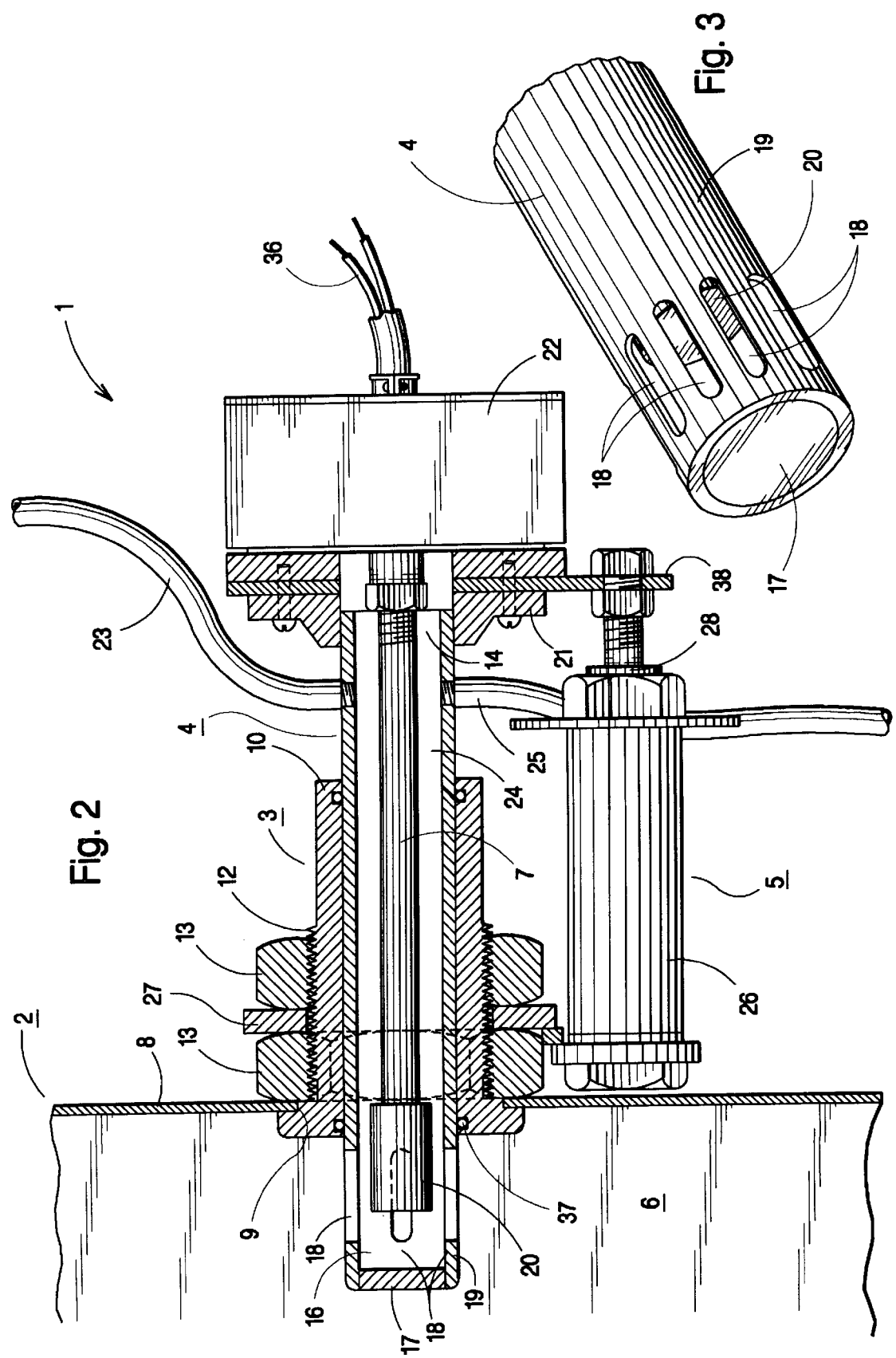

RETRACTABLE HUMIDITY SENSOR FOR USE IN CORROSION TEST CHAMBERS

BACKGROUND OF THE INVENTION

This invention is related to apparatus for conducting corrosion tests on various materials, and in particular, it is directed to improved apparatus for positioning and shielding sensor probes used to control atmosphere within a corrosion test chamber.

It is well known in the art of corrosion testing that test chambers are equipped with humidity probes to monitor and control relative humidity within the chamber. Such humidity probes are often problematic because they are fixed-in-place within the test chamber where they are continuously exposed to high humidity and salt fog or spray that is used to determine the corrosion resistance of various materials. Current state-of-the-art sensor probes are unable to withstand the affects of such hostile environments. Salt spray deposits from the fog buildup on the sensor probes can cause complete probe failure. In such instances, probe replacement is necessary to continue testing. The probes can also become wet from the high humidity inside the test chamber, up to 100% relative humidity. In this instance, the wet probe will either fail to send signals, or send unreliable signals to the chamber controller. Such wet probes must be removed from the test chamber for complete drying and cleaning to make them suitable for reuse. Accordingly, service life for past corrosion test humidity probe devices has been short, and the necessary maintenance to maintain such probes in a clean and dry reliable condition interrupts corrosion testing.

In the past, there have been attempts to overcome the aforementioned sensor probe problems. For example, in U.S. Pat. No. 4,794,804, Ishii teaches that corrosion test salt spray " . . . adheres to the humidity sensor provided in the test chamber, making it impossible to perform humidity measurements." Ishii attempts to solve this problem by using a probe shield that includes a box like probe container having a hinged lid that covers a humidity probe positioned within the container. The probe container is attached to an inside wall of the test chamber, and the fixed-in-place humidity probe is shielded from or exposed to test chamber environment by either rotating the hinged lid to a closed position or rotating the hinged lid to an open position. However, when Ishii rotates his lid to an open position, the interior of his box is exposed to whatever condition may exist within the test chamber. His open lid greatly increases the chance for residual salt and moisture to enter and adhere to the inside surfaces of his box, and this increases the likelihood for sensor contamination and failure.

Another attempt to improve sensor probe reliability is disclosed in an undated drawing labeled Exhibit A listed on PTO-FORM 1449 of the instant application. The probe arrangement shown in the drawing was designed by Atotech USA Inc., during the 1980's when Atotech was known as The Harshaw Chemical Company. Atotech has disclosed that during about the year 1987, a single probe device, as shown in Exhibit A, was built and sold to a Harshaw customer. No subsequent probes or sales were ever made after that first sale date.

As disclosed by Atotech, and referring to Exhibit A, the Harshaw drawing shows a probe assembly 1 attached to a test chamber wall 2 and a drive 3 to extend or retract a sensor probe 4 relative to the inside space 5 of the chamber. The probe assembly includes a first PVC pipe 6 attached to and extending through the chamber wall 2 and a second concentric PVC pipe 7 moveably mounted within pipe 6. Drive 3 is attached to pipe 7 via a mounting plate 8 to move pipe 6 toward or away from the inside space 5 of the chamber, and the sensor probe 4 is fixed to plate 8 to follow the movement of the pipe. The sensor probe extends along the inside length of both pipes and is spaced apart from the inside walls 6a and 7a of pipes to prevent unnecessary contact with the delicate sensor prove surface. The Harshaw arrangement enables operators to insert or remove the sensor tip 9 with respect to chamber space 5. However, when the sensor tip is inserted into chamber space 5, to monitor chamber conditions, seal plate 10 is moved away from pipe 6 to expose the inside diameter 6a to the atmosphere within the chamber. This condition is similar to Ishii where the inside surfaces are now open to contamination by residual salt and moisture from the chamber and possible probe failure.

Such probe shielding devices of the past have failed to provide adequate protection against hostile environment within a corrosion test chamber, and such shielded probes continue to be prone to premature failure and short service life. For example, referring again to Ishii's humidity probe arrangement, the probe arrangement fails to provide any means for removing the humidity probe from the corrosion test chamber when the chamber environment is not being monitored by the probe, for instance during salt fogging cycles. And even though the humidity probe is shielded within the container, at such times, the humidity probe is still exposed to the high humidity produced during salt fogging, about 100% relative humidity. High humidity can cause condensation to form on the sensitive probe tip housed within the container, and the wet probe tip will produce faulty signals to the chamber controller during the next chamber monitoring cycle. Ishii's humidity probe can also be exposed to small amounts of salt water that seep into the container during a salt fogging cycle, or to salt water that drips onto the probe when the wet lid is rotated to an open position after fogging. Consequently, such condensation and salt buildup will cause the probe to either completely fail or send unreliable signals to the chamber controller. Again, such conditions make it necessary to discontinue the corrosion test activity to remove the contaminated probe from the chamber for either drying, cleaning, or replacement of the probe.

SUMMARY OF THE INVENTION

It is therefore an object of this invention to provide a sensor probe device that can be selectively removed from an active chamber space.

It is a further object of this invention to provide a sensor probe device that can be selectively inserted into an active chamber space.

It is still a further object of this invention to provide a sensor probe device having an air purge system for maintaining probe integrity.

Finally, it is an object of this invention to provide a movable sensor probe device having apparatus to provide an air wipe shield for maintaining probe integrity.

In satisfaction of the foregoing objects and advantages, the present invention provides a sensor probe device for monitoring atmosphere within a chamber. The device includes a housing that extends through a wall of the chamber being monitored, and a tubular sleeve that is movably captured within the housing. The sleeve includes an open end for receiving a sensor probe, and a closed end having a plurality of radially spaced apertures that extend through the sleeve wall. The apertures provide an open ribbed portion that exposes the enclosed sensor probe to chamber atmosphere when the sleeve portion is inserted into the chamber. A drive mechanism is attached to either extend the open ribbed portion of the sleeve outward from its shielded position within the housing to an extended position within the chamber, or retract the sleeve portion from the chamber back into its shielded position within the housing. An air supply is provided to inject forced air into the sleeve to maintain sensor probe integrity by purging contaminates through a drain in the sleeve wall, and an external air wipe nozzle is attached to the closed end of the sleeve to provide an air flow along the sleeve to prevent chamber atmosphere from entering the sleeve through the radially spaced apertures.

BRIEF DESCRIPTION OF THE DRAWINGS

FIG. 2. is a cross-section similar to FIG. 1 showing the preferred sensor probe device shown in an extended position within the chamber.

FIG. 3. is an enlarged isometric view showing the sensor tip of the sensor probe device.

DETAILED DESCRIPTION OF THE PREFERRED EMBODIMENT

Figure 1:
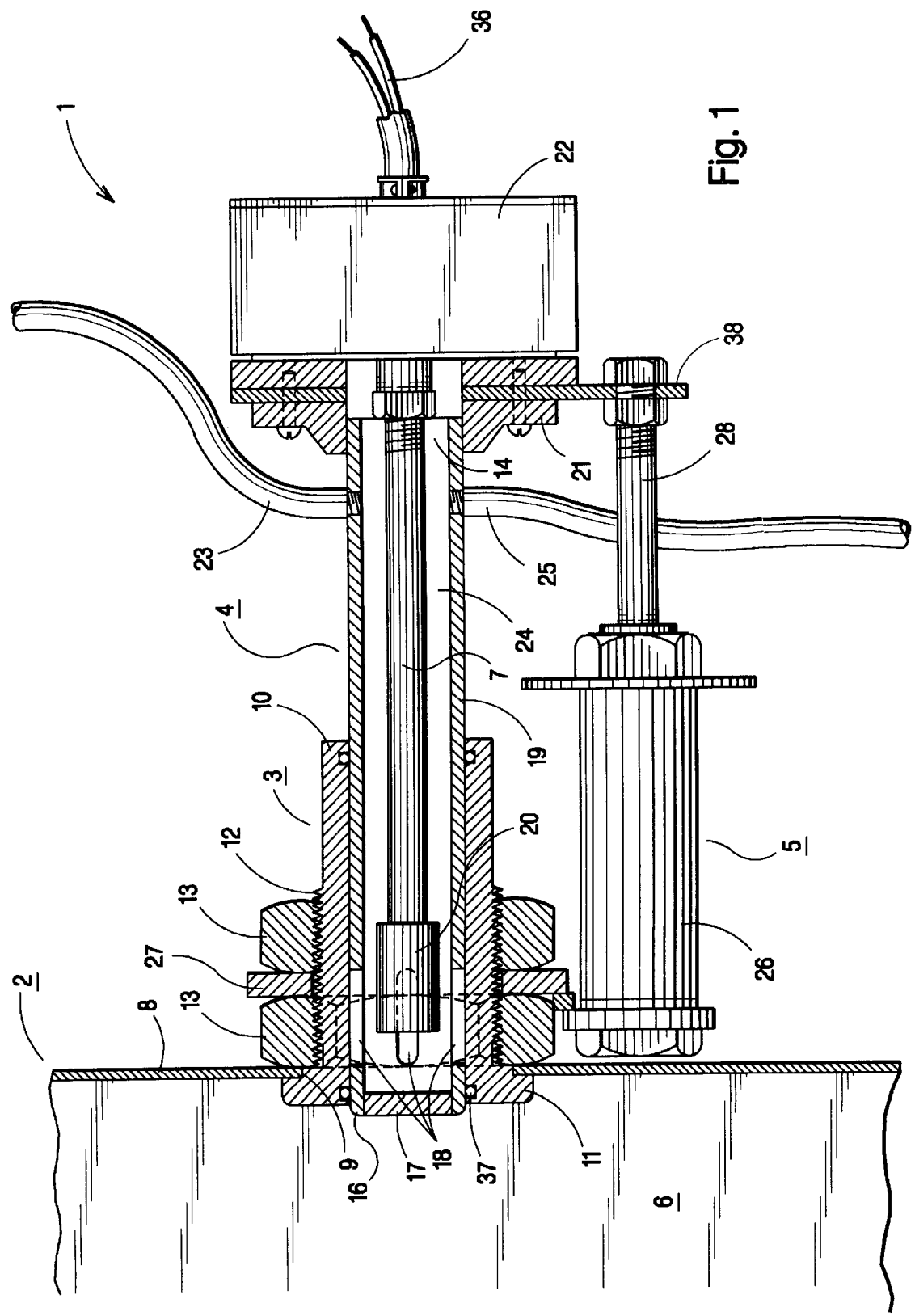
FIG. 1. is a cross-section showing the preferred sensor probe device in a retracted position outside the chamber.

Referring to FIG. 1 of the drawings, the preferred sensor probe device 1 is shown attached to a wall of a chamber 2. The sensor device includes a housing 3, a tubular sleeve 4 and a drive mechanism 5. The drive mechanism is provided to either selectively extend or retract sleeve 4 relative to an interior space 6 within the chamber 2.

In the preferred embodiment, the sensor device 1 houses a humidity probe for monitoring the relative humidity inside a corrosion test chamber 2. At least one wall 8 of the test chamber includes at least one aperture 9 for receiving the sensor probe device 1, shown attached to the chamber by fixing housing 3 to wall 8 of the chamber. Housing 3 includes an elongated portion 10, that extends through aperture 9, and an enlarged end or shoulder 11 that engages the inside surface of the chamber wall 8. Housing 3 further includes a threaded section 12 that extends along a length of the elongated portion 10. The threaded section 12 extends outward from shoulder 11, through aperture 9, and is fixed to wall 8 by lock nuts 13.

The tubular sleeve 4 extends along the inside length of housing 3 and sleeve 4 is sized to provide a sliding fit between the inside surface 3a and outside surface 4a of the housing and sleeve respectively. Tubular sleeve 4 further includes an open end 14 for receiving any desired sensor probe, for example in the preferred embodiment a humidity probe 7, and a closed end 16 having a plug 17. A plurality of radially spaced apart apertures or slots 18, shown more clearly in FIG. 3, extend through sleeve wall 19 proximate the closed end 16, and the humidity probe 7 is placed within sleeve 4 to position its probe tip 20 adjacent the radially spaced apertures 18. As shown in FIG. 2, the placement of the humidity probe, or any other desired sensor probe, exposes the probe tip 20 to chamber atmosphere when the movable sleeve 4 is extended to position the apertures 18 within chamber space 6. Sleeve 4 further includes a mounting plate 21 attached to electrical box 22 to connect the sensor probe wires 36 to a programmable controller (not shown) that controls a test program for the chamber.

At least one air supply 23 is attached to sleeve 4 to inject forced air into the interior space 24 of sleeve 4. The air supply line 23 is attached to an air supply (not shown) to inject forced air into space 24. The forced air purges any contamination, such as condensation or accumulated solids from the sleeve interior through a sleeve drain 25 located in a lower portion of the sleeve wall. The forced air flow also maintains the sensor tip, housed within the probe tip 20, in a dry condition during monitoring of the chamber atmosphere. This insures sending accurate probe signals to the chamber controller.

The drive mechanism 5 comprises a pneumatic cylinder with its cylinder end 26 attached to the housing 3 via a mounting plate 27 captured between the lock nuts 13 that fasten housing 3 to the chamber wall 8. The cylinder piston rod 28 is fastened to plate 38 attached to mounting plate 27 of sleeve 4. The pneumatic cylinder arrangement provides one drive means for selectively retracting sleeve 4 from chamber space 6 when the chamber atmosphere isn't being monitored by the probe 7. The cylinder is activated to extend its piston rod 28 and withdraw sleeve 4 from the chamber space 6 to a shielded position within housing 3 as shown in FIG. 1. The pneumatic cylinder is reversed to extend sleeve 4 outward from its shielded position in housing 3, back into chamber space 6 as shown in FIG. 2. It should be understood, however, that any suitable drive mechanism known in the art may be used to extend and retract sleeve 4 without departing from the scope of this invention. For example, either an electrical solenoid, or a motor and gear arrangement may be substituted for the pneumatic cylinder 5.

Figure 4:
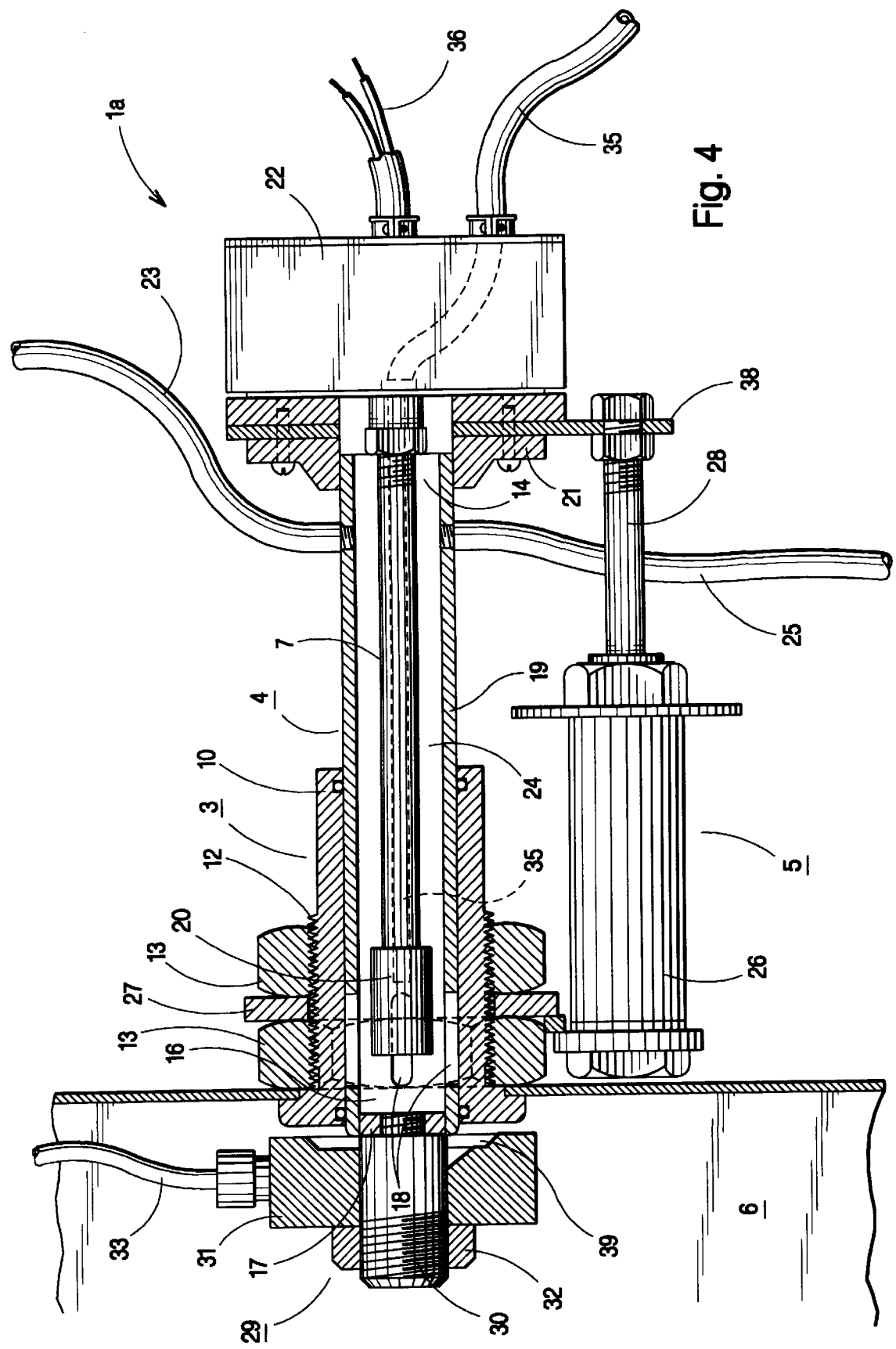
FIG. 4. is a cross-section similar to FIG. 1 showing an alternate embodiment having an air wipe system attached to the sensor probe device.
Figure 5:
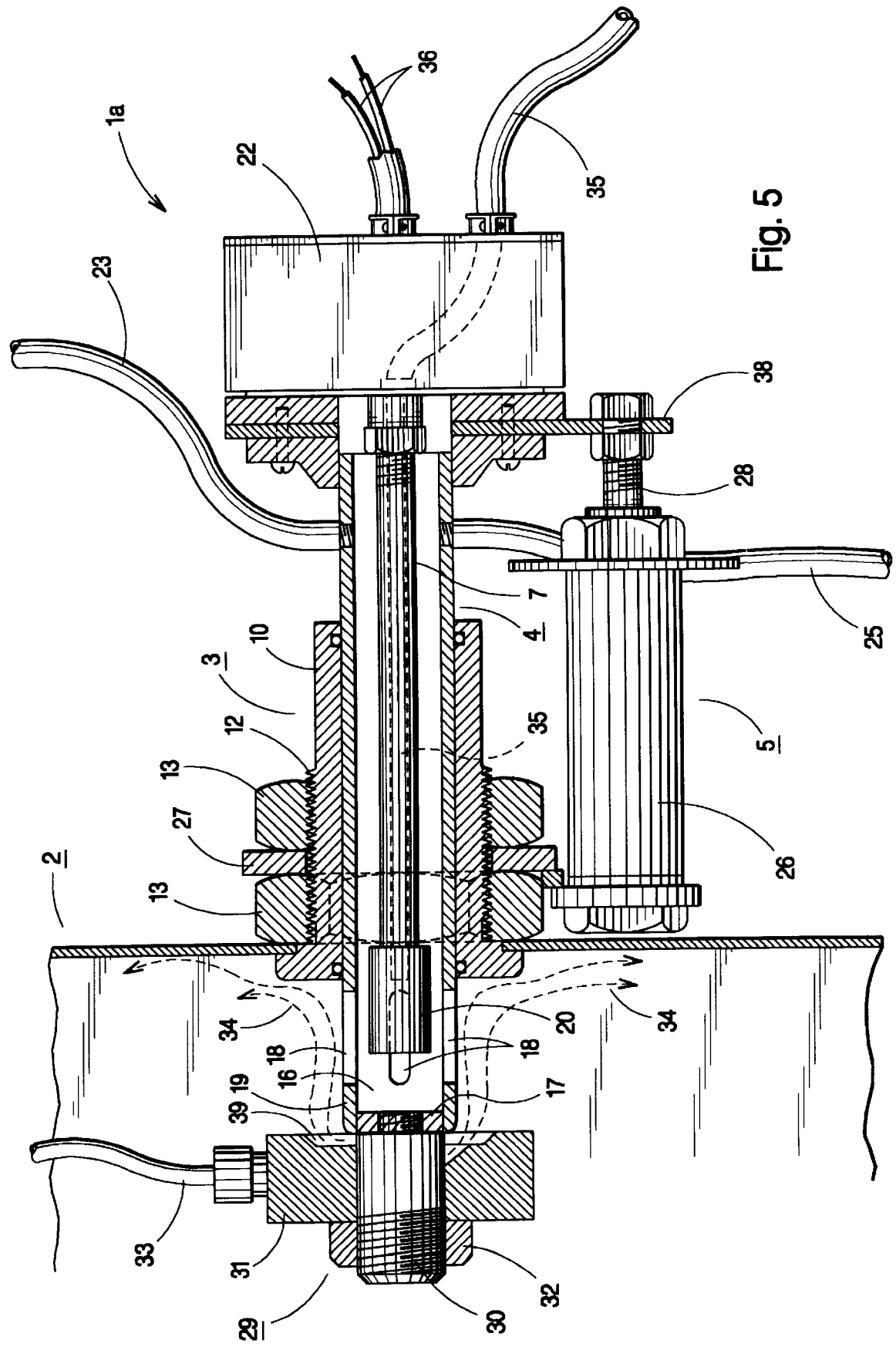
FIG. 5. is a cross-section similar to FIG. 4 showing the alternate embodiment of the present invention in its extended position within the chamber.

In an alternate embodiment of the sensor probe device invention, shown in FIGS. 4 and 5, the sensor device 1a includes an air wipe assembly 29 attached to the closed end portion 16 of sleeve 4. The air wipe assembly includes a mounting block 30 fastened to plug 17 of sleeve 4, and an air wipe nozzle 31 coupled to mounting block 30 by a threaded fastener as shown at 32, or any other suitable fastener means such as a speed nut. An air supply 33 is attached to the air wipe nozzle to selectively bathe the closed end portion of sleeve 4 with a flow of air 34 across apertures 18 to shield the sensitive probe tip 19 from the chamber atmosphere. Referring again to the alternate embodiment, a second air supply 35 is shown extending along the interior length of probe 7 to deliver an additional forced air flow to the sensor tip in end 20 and purge any moisture that may accumulate within the sensor probe 7. Air line 35 is also attached to an air supply (not shown) to inject a forced air flow toward the probe tip end 20. This additional air flow further insures that the portion of the wires 36, located inside the probe assembly 7 and 20, are maintained in a dry, clean condition for monitoring operations. As clearly shown in FIGS. 4 and 5, the second air supply line 35 is attached to electrical box 22, for example by a cable connector. Air line 35 extends through box 22, along the interior length of probe 7, and ends at a location proximate the spliced ends of the probe wires 36 (the sensor tip) located in the sensor tip end portion 20 of the probe assembly.

Corrosion testing typically includes subjecting selected test specimens through a programmed test cycle where the test chamber environment is controlled by a computer from one test stage to another test stage, for example, through water fog, salt spray, and dry stages. During a dry stage, the controller is programmed to generate a signal that causes drive mechanism 5 to retract its piston rod 28 and extend sleeve 4 outward from its shielded position within housing 3 and into the chamber space 6, as shown in FIGS. 2 and 5. In this extended position, the tip end portion 20 of the humidity probe is exposed to atmospheric conditions within the test chamber by way of the apertures 18 extending through the sleeve wall 19. As heretofore mentioned, any sensor probe capable of generating an electrical signal can be used to monitor the test chamber space 6, for example, a humidity probe, a temperature probe or the like. The sensor probe signals are continually sent from the extended sensor tip in end 20 to a programmable controller through the wires 36 that extend from box 22. The programmed controller responds to the generated probe signals by sending a responsive signal to a moisture dispensing device, for example, a water fogger or the like, that adds moisture to the test chamber space 6. The controller can be programmed to any predetermined desired humidity level for the dry stage, within a range of say about 30% to 95% relative humidity, and for example, about a 50% preferred relative humidity. The chamber controller then maintains the preselected 50% relative humidity by sending a responsive signal that causes the moisture dispensing device to either add or discontinue adding moisture to the interior space 6 of the test chamber. In addition, if the alternate air wipe embodiment shown in FIGS. 4 and 5 is provided, the controller can also send a simultaneous signal to the air supply (not shown) to discharge a flow of air from the air wipe nozzle orifice 39 positioned adjacent the closed end of sleeve 4. The forced airflow issuing from orifice 39, shown by the arrows 34 in FIG. 5, provides an air wipe that envelops a length of sleeve 4. The air wipe flows across the apertures 18 to provide a barrier that prevents the above-mentioned dispensed moisture from entering the sleeve through the apertures where it would contaminate the sensor tip in end 20 housed within the sleeve 4.

When the programmed corrosion test cycle initiates either a water fog stage where relative humidity is about 100%, or a salt spray stage where relative humidity can be 100% or less, the programmed controller generates a signal that extends piston rod 28 and withdraws sleeve 4 from the interior space 6 and back into a retracted position within housing 3 and outside the chamber as shown in either FIG. 1 or FIG. 4. In its retracted position, sleeve 4 is movably captured within housing 3 and its plug end 17 engages O-ring 37 in housing 3 to seal off and shield the apertures 18, and sensitive tip in end 20, from the now hostile environment within the corrosion test chamber. The combination of the O-ring and the sliding fit between surfaces 3a and 4a of the housing and sleeve, effectively prevent any residual salts or moisture from entering the interior surfaces within the housing 3. Additionally O-ring 37 provides a wiper that removes any salt or moisture that may adhere to the surface of the sleeve as it is being withdrawn back into the housing and thereby further reduces the likelihood of carrying contamination into the housing.

Sleeve 4 remains in its shielded position within the housing until the test cycle program initiates another dry stage in the test cycle. Then, as before, the controller sends a signal to the drive mechanism 5 to extend movable sleeve 4 back into the test chamber space 6 to control relative humidity during the next dry stage.

While this invention has been described as having a preferred design, it is understood that it is capable of further modifications, uses, and/or adaptations following in general the principle of the invention and including such departures from the present disclosure as come within known or customary practice in the art to which the invention pertains, and as may be applied to the essential features set forth herein, and fall within the scope of the invention limited by the appended claims. For example, although the preferred embodiment shows a humidity probe attached to a wall of a corrosion test chamber, it should be understood that the present invention can be used to monitor any interior space with any desired type sensor probe, for example, a thermocouple for temperature measurements, without departing from the scope of this invention.

We claim:

1. Apparatus for monitoring atmosphere within a chamber comprising:
    a) a housing having one end communicating with the chamber;
    b) a sensor probe slidably supported within said housing;
    c) a drive mechanism attached to said sensor probe to extend said sensor probe outward from said housing to a monitoring position within the chamber and to retract said sensor probe inward to a stored position within said housing; and
    d) a seal positioned to close said housing end that communicates with the chamber when said sensor probe is retracted to the stored position within said housing, said closed housing end shielding said stored sensor probe from the atmosphere within the chamber.

2. The invention recited in claim 1 wherein said sensor probe engages a seal in said housing to shield said sensor probe from the atmosphere within the chamber when said sensor probe is retracted to the stored position within said housing.

3. The invention recited in claim 1 wherein said sensor probe is a tube having a first end that communicates with said chamber when said sensor probe is extended to said monitoring position, said first end containing a sensor therein and including a plurality of radially spaced apart apertures extending through a wall of said tube to expose said sensor to chamber atmosphere.

4. The invention recited in claim 3 where said radially spaced apart apertures are elongated slots extending along a length of said tube.

5. The invention recited in claim 1 including an air purge comprising:
    a) at least one air supply line extending through a wall of said sensor probe; and
    b) at least one drain extending through said wall.

6. The invention recited in claim 5 wherein said at least one air supply line is attached to a regulated air supply to selectively inject forced air into a space within said sensor probe.

7. The invention recited in claim 6 wherein said drain is positioned to expel contaminates and forced air from said space within said sensor probe.

8. The invention recited in claim 5 including a second air purge comprising:
    a) at least one air supply line communicating with a space within said sensor probe; and
    b) a regulated air supply attached to said air supply line to selectively inject forced air into said space within said sensor probe.

9. The invention recited in claim 8 wherein said at least one air supply line is positioned to inject forced air adjacent a sensor located within said sensor probe.

10. The invention recited in claim 1 including an air wipe apparatus comprising:

a) a nozzle attached to said sensor probe;

b) an orifice in said air nozzle shaped to provide an air flow that envelops a length of said sensor probe with an air wipe; and c) an air supply attached to said air nozzle to provide a supply of air that is discharged through the orifice of said nozzle.

11. The invention recited in claim 10 wherein said air wipe envelops at least one aperture that extends through a wall of said sensor probe to communicate with a space therein.

12. The invention recited in claim 1 comprising:

a) an air purge having:
  i) at least one air supply line extending through a wall of said sensor probe;
  ii) at least one drain extending through said wall;
  iii) a regulated air supply attached to said at least one air supply line to selectively inject forced air into a space within said sensor probe; and b) an air wipe apparatus comprising:
  i) a nozzle attached to a first end of said sensor probe;
  ii) an orifice in said air nozzle shaped to provide an air flow that envelops a length of said sensor probe with an air wipe;
  iii) an air supply attached to said air nozzle to provide a supply of air that is discharged through the orifice of said nozzle.

13. The invention recited in claim 12 including a second air purge comprising:

a) at least one air supply line communicating with a space within said sensor probe; and b) a regulated air supply attached to said air supply line to selectively inject forced air into said space within said sensor probe.

* * * * *